United States Patent
Zemel et al.

(10) Patent No.: US 8,413,502 B2
(45) Date of Patent: Apr. 9, 2013

(54) DEVICE FOR MEASURING INFANT FEEDING PERFORMANCE

(75) Inventors: Jay N. Zemel, Jenkintown, PA (US); Barbara Medoff-Cooper, Bala Cynwyd, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/920,178

(22) PCT Filed: Apr. 27, 2009

(86) PCT No.: PCT/US2009/041782
§ 371 (c)(1), (2), (4) Date: Dec. 15, 2010

(87) PCT Pub. No.: WO2009/132334
PCT Pub. Date: Oct. 29, 2009

(65) Prior Publication Data
US 2011/0087078 A1    Apr. 14, 2011

Related U.S. Application Data

(60) Provisional application No. 61/047,995, filed on Apr. 25, 2008.

(51) Int. Cl.
*G01F 15/02* (2006.01)
(52) U.S. Cl.
USPC .......................................................... 73/198
(58) Field of Classification Search .............. 73/198, 73/37; 604/67
See application file for complete search history.

(56) References Cited

U.S. PATENT DOCUMENTS

| | | | |
|---|---|---|---|
| 3,790,016 A | 2/1974 | Kron | |
| 3,895,533 A * | 7/1975 | Steier | 600/587 |
| 4,232,687 A | 11/1980 | Anderson-Shanklin | |
| 4,376,053 A | 3/1983 | Bullock et al. | |
| 4,627,271 A | 12/1986 | Abbott et al. | |
| 6,033,367 A | 3/2000 | Goldfield | |
| 6,109,100 A * | 8/2000 | Buckley et al. | 73/198 |
| 6,283,719 B1 | 9/2001 | Frantz et al. | |
| 6,588,613 B1 | 7/2003 | Pechenik et al. | |
| 6,966,904 B2 | 11/2005 | Ruth et al. | |
| 7,333,020 B2 * | 2/2008 | Cohen et al. | 340/573.1 |

(Continued)

OTHER PUBLICATIONS

Woolridge, et al., "The Continuous Measurement of Milk Intake at a Feed in Breastfed Babies", Early Human Development, Sep. 1982, pp. 365-373.

(Continued)

*Primary Examiner* — Jewel V Thompson
(74) *Attorney, Agent, or Firm* — RatnerPrestia

(57) ABSTRACT

Devices, systems and methods for measuring infant feeding performance. The device includes a body portion, a pressure sensor and an integrated circuit. The body portion includes a first end for receiving a fluid, a second end mateable with a feeding nipple, and a conduit in fluid communication with the first and second ends. The pressure sensor is disposed in the body portion, is in contact with the fluid in the conduit, and generates a signal representing a pressure of the fluid passing through the conduit during a feeding session. The integrated circuit is disposed in the body portion and is electrically connected to the pressure sensor. The integrated circuit receives the pressure signal and determines a feeding factor over the feeding session indicative of the infant feeding performance.

25 Claims, 8 Drawing Sheets

U.S. PATENT DOCUMENTS

| | | | |
|---|---|---|---|
| 7,896,835 B2* | 3/2011 | Dahan et al. | 604/76 |
| 2001/0044588 A1 | 11/2001 | Mault | |
| 2006/0074354 A1 | 4/2006 | Barlow et al. | |
| 2008/0039778 A1* | 2/2008 | Goldie et al. | 604/67 |

OTHER PUBLICATIONS

Kron, et al., A Method of Measuring Sucking Behavior of Newborn Infants, Psychosomatic Medicine, Mar./Apr. 1963, pp. 181-191.

International Search Report dated Jun. 29, 2009.

Gewolb et al., "Developmental Patterns of Rhythmic Suck and Swallow in Preterm Infants", Developmental Medicine & Child neurology, vol. 43, pp. 22-27, 2001.

Mizuno et al., "Neonatal Feeding Performance as a Predictor of Neurodevelopmental Outcome at 18 Months", Developmental Medicine & Child Neurology, vol. 47, pp. 299-304, 2005.

Office Action for U.S. Appl. No. 12/595,755, mailed Sep. 6, 2012.

\* cited by examiner

DEVICE FOR MEASURING INFANT FEEDING PERFORMANCE

The present application claims the benefit of priority of PCT International Application No. PCT/US2009/041782 filed Apr. 27, 2009 which claims the benefit from U.S. provisional application No. 61/047,995 the contents of which are incorporated herein by reference.

STATEMENT REGARDING FEDERALLY SPONSORED RESEARCH

This invention was made with partial government support under the grant R01-NR02093 awarded by the National Institutes of Health. The government has certain rights in the invention.

FIELD OF THE INVENTION

This present invention relates to measurement of a feeding performance of an infant. More particularly, the present invention relates to devices and systems for measuring an infant's feeding responsiveness based on sucking pressure and/or fluid volumetric flow induced by the infant on a feeding apparatus.

BACKGROUND OF THE INVENTION

Devices for assessing infant feeding performance by quantitatively measuring certain aspects of infant feeding are known. For example, U.S. Pat. No. 3,895,533 to Steier discloses a device resembling a baby bottle for measuring the negative sucking pressure of an infant to determine if the baby has a relatively poor sucking ability. U.S. Pat. No. 4,232,687 to Anderson-Shanklin discloses a feeding nipple apparatus for measuring the negative sucking pressure and expression pressure that an infant exerts on a test nipple. The apparatus measures an infant's (in particular a premature infant's) capacity to bottle feed in order to mitigate the risk of regurgitation or milk aspiration. Another device is shown in U.S. Pat. No. 6,033,367 to Goldfield which discloses a system for diagnosing and/or monitoring sucking, swallowing, and breathing competence of an impaired neonate or postoperative infant. The system of Goldfield involves sensors for measuring negative sucking pressure and breathing rate, as well as an automated valve and computerized feedback loop to control the amount of fluid flowing through a feeding nipple to an infant as a function of the infant negative sucking pressure and breathing rate.

U.S. Pat. No. 6,109,100 to Buckley et al. describes a baby bottle attachment that incorporates a pressure sensor, and optionally, a flow meter. This attachment is tethered to a remote signal processing and recording device, such as a data logger or computer. According to Buckley et al., a signal from the pressure sensor is sent to the recording device where it is processed into data, which can be observed by a nurse, parent, or other individual. Alternatively, the data compiled by the computer can be transmitted wirelessly to a small, portable receiving device, such as a cell phone.

Notwithstanding these efforts, there remains a need for a device that can conveniently and accurately measure an infant's responsiveness during feeding. More specifically, there is a need for a small, easily-handled device that, independently of a remote system, has a capacity for generating and recording data pertaining to the sucking, behavioral, and/or physiological characteristics or descriptors related to feeding responsiveness. Additionally, there remains a need for a measuring device that can be easily disassembled, cleaned, and reassembled.

SUMMARY OF THE INVENTION

A method of measuring infant feeding performance includes passing fluid to a feeding nipple through a conduit. The conduit has a first section to receive the fluid and a second section to pass the fluid to the feeding nipple, where the first section has a different cross-sectional area from the second section. The method also includes monitoring a pressure of the fluid passing through the conduit during a feeding session at a position in the conduit between the first section and the second section and determining a feeding factor from the monitored pressure over the feeding session indicative of the infant feeding performance.

A device for measuring infant feeding performance includes a body portion, a pressure sensor and an integrated circuit. The body portion has a first end for receiving a fluid, a second end mateable with a feeding nipple, and a conduit in fluid communication with the first end and the second end. The pressure sensor is disposed in the body portion and is in contact with the fluid in the conduit. The pressure sensor is configured to generate a signal representing a pressure of the fluid passing through the conduit during a feeding session. The integrated circuit is disposed in the body portion and is electrically connected to the pressure sensor. The integrated circuit is configured to receive the pressure signal and to determine a feeding factor over the feeding session indicative of the infant feeding performance.

A system for measuring infant feeding performance includes a fluid source for storing a comestible fluid, a feeding nipple, a body portion disposed between and coupled to the fluid source and to the feeding nipple, a pressure sensor and an electronics system. The body portion includes a conduit in fluid communication with the fluid source and the feeding nipple. The pressure sensor is disposed within the body portion and is configured to generate a signal representing a pressure of the fluid passing through the conduit. The electronics system is embedded within the body portion and is electrically connected to the pressure sensor. The electronics system is configured to receive the pressure signal and to determine at least one of a sucking pressure response and a fluid volumetric flow response indicative of the infant feeding performance.

A method of manufacturing a device for measuring infant feeding performance includes forming a body portion having a first end mateable with a fluid source, a second end mateable with a feeding nipple, and a conduit in fluid communication with the first end and the second end; providing a pressure sensor assembly within the body portion to be in contact with fluid in the conduit, where the pressure sensor is configured to generate a signal representing a pressure of the fluid in the conduit; and providing an integrated circuit within the body portion such that the integrated circuit is electrically connected to the pressure sensor assembly. The conduit includes a first conduit section for receiving the fluid from the fluid source and a second conduit section for passing the fluid to the feeding nipple, where the second conduit section has a cross-sectional area greater than a cross-sectional area of the first conduit section. The integrated circuit is configured to receive the pressure signal and to determine at least one of a sucking pressure response and a fluid volumetric flow response.

DETAILED DESCRIPTION OF THE INVENTION

Aspects of the present invention include an independent, hand-held device having primary application for measuring, recording, and optionally monitoring one or more feeding factors related to feeding performance of an infant, for example, during a feeding session. To measure one or more feeding factors, an exemplary device includes embedded electronics including at least one sensor and a computerized data processing system. In one embodiment, the device includes an embedded microcontroller and at least one embedded sensor, such as a pressure sensor, for measuring and recording a feeding factor, such as sucking pressure, within and fluid volumetric flow through the device. For example, when used in conjunction with a feeding nipple and a fluid reservoir holding a comestible fluid (e.g., a baby bottle containing infant formula, expressed breast milk, pediatric electrolyte solution, or the like) the device may measure and record the sucking response exhibited by an infant. It is contemplated that the exemplary device may function independently of an external system for data collection, recording, and/or analysis.

A feeding session refers to a continuous period of time during which an infant (i.e., a human child from age birth to about one-year old) is provided with a feeding device, such as a baby bottle, and is encouraged to feed from the device. The feeding session may be a function of a predetermined period of time, a predetermined consumption volume, or both. A feeding performance of the infant may be determined during the feeding session. The feeding session also can be subdivided into two or more epochs to further quantify the feeding performance of an infant. Feeding sessions also can be subdivided in relation to one or more events or markers such as an instance of particular behavior demonstrated by the observed infant.

Feeding performance refers to an infant's innate or acquired capacity for orally feeding via a synthetic nipple, expressed as physical, physiological and/or behavioral responses during a feeding session. Feeding factors relate to one or more physical, physiological, and/or behavioral responses produced or exhibited by an infant while orally feeding or attempting to orally feed. Examples of feeding factors include sucking pressure, expression pressure, oxygen saturation level, swallowing, respiration, and the like.

Figure 8:
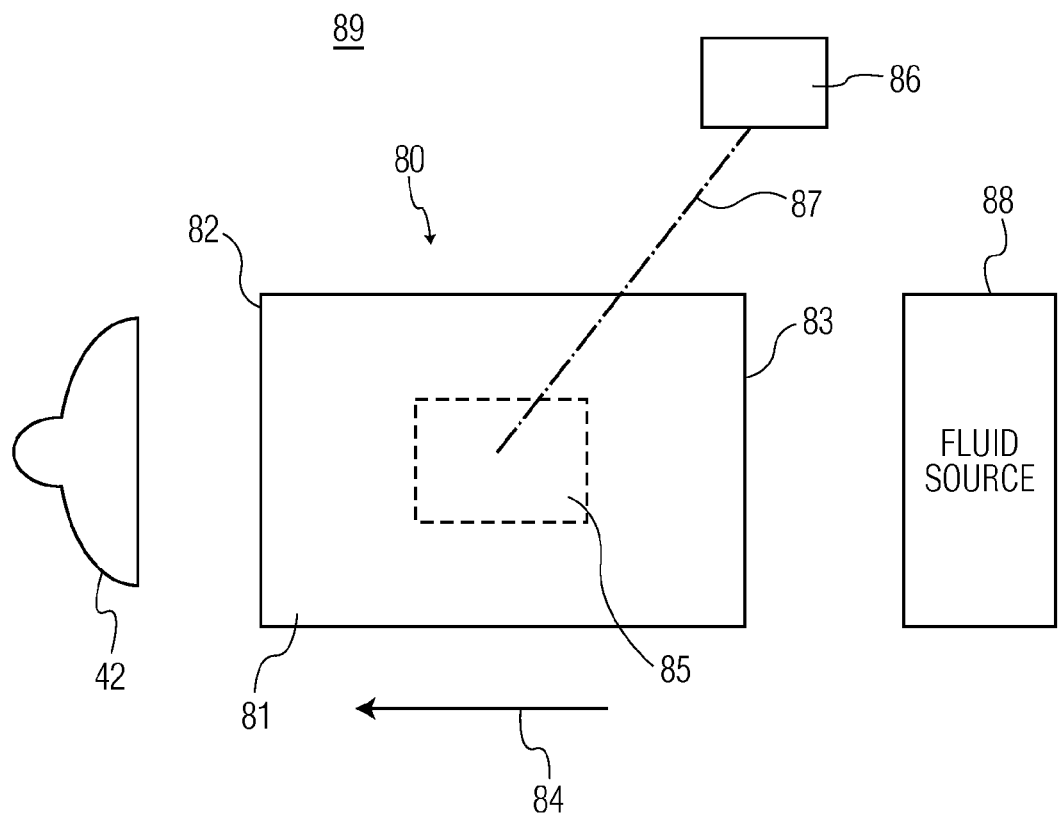
FIG. 8 is a structural view diagram of an exemplary system for measuring infant feeding performance, according to an embodiment of the present invention.

Referring to FIG. 8, a structural view diagram of an exemplary system 89 for measuring infant feeding performance. System 89 includes device 80 for measuring at least one feeding factor, nipple 42 and fluid source 88. Device 80 includes a body portion 81, a fluid inlet side 83 coupled to fluid source 88 and a fluid outlet side 82, coupled to nipple 42, and defining a fluid flow direction 84. Device 80 includes measurement/monitoring system 85 for measuring, recording, and optionally monitoring at least one feeding factor. As described further below, measurement/monitoring system 85 may include an embedded sensor, a microcontroller, and a memory chip (not shown). Device 80 may also include optional external sensor 86 for measuring one or more additional feeding factors, and an optional data communication link 87 for transmitting data between and/or receiving data from the optional external sensor 86 or an external data recording/data processing device (not shown).

As used herein, the term electronics relates to devices and systems that utilize the conductive or semiconductive flow of electricity and may include electronic sensors, microprocessors, microcontrollers, printed circuit boards, signal amplifiers, analog to digital converters, microelectromechanical systems, memory chips, electronic displays, microphones, electrical relays, switches, transceivers, and the like. Transceivers may include wired transceivers and wireless transceivers (e.g., Bluetooth devices).

As used herein, the term sensor relates to a device which measures a physical quantity, and converts it into an electrical signal, preferably a digital signal. The analog signal may be read by an instrument which may, for example, include a separate analog to digital converter (ADC), a microprocessor or a microcontroller. Examples of sensors include photoelectric elements, piezoresistors, piezoelectrics, pyroelectrics, thermistors and pulse oximeters utilizing infrared sources, microphones for use in recording comments during a feeding session, as well as fiber optic elements for measuring temperature, pressure, and strain.

As used herein, the term embedded relates to being contained within the confines of an article, including the article's interior and surface, or positioned on the outer surface of the article. Embedded electronics are contrasted with remote or external electronics which are outside the confines of the article, regardless of whether the electronics are in electronic communication with the article via a wired or wireless data transfer system.

For illustrative purposes, embodiments of the present invention having a pressure sensor for measuring sucking pressure are described below with reference to FIGS. 1-10B. It is understood however, that in other embodiments, the embedded electronics may include alternative or supplemental sensors for measuring other feeding factors.

Figure 1:
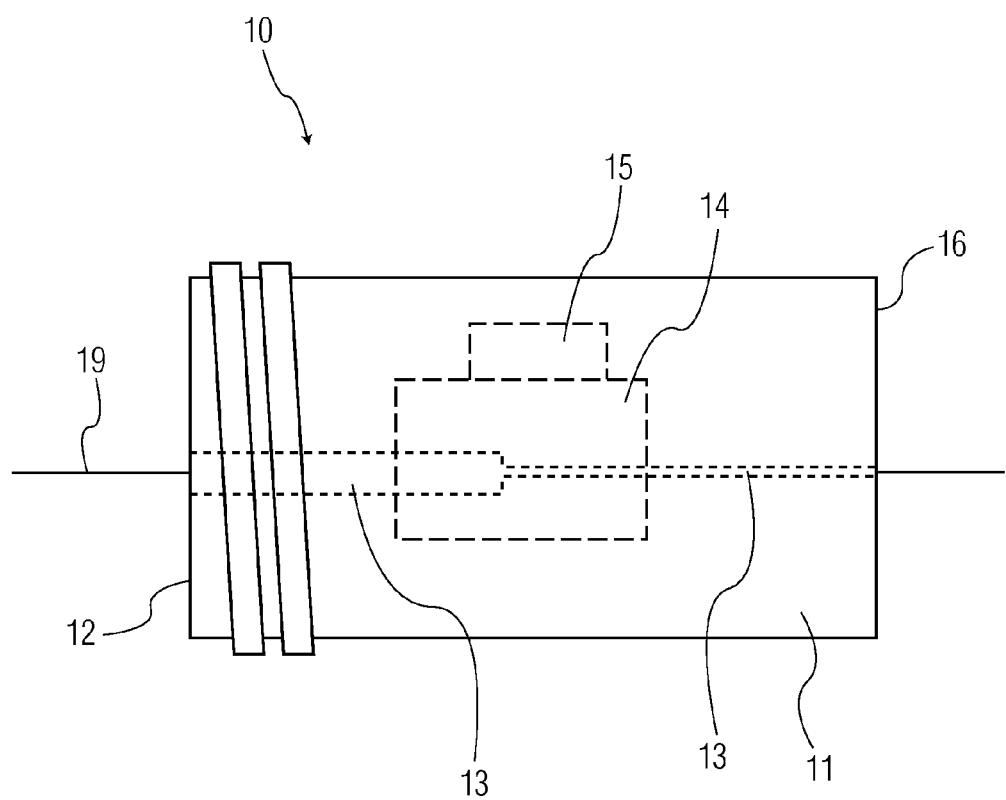
FIG. 1 is a side view diagram of an exemplary device for measuring infant feeding performance, according to an embodiment of the present invention.

FIG. 1 illustrates a simplified embodiment in accordance with the present invention having primary application for measuring, recording, and optionally monitoring the pressure and flow of a comestible fluid, such as infant formula, expressed breast milk, or pediatric electrolyte solution, through a measuring device as a function of time.

FIG. 1 is a side view diagram of an exemplary device 10 for measuring infant feeding performance. Device 10 includes body portion 11 having a first end 16 adapted to receive a fluid from a fluid source, such as a conventional baby bottle (not shown), a second end 12 adapted to connect to an infant feeding nipple (not shown), and a hollow conduit 13 in fluid communication with respective first and second ends 16, 12. Device 10 also includes a pressure sensor 14 for monitoring pressure in conduit 13 and integrated circuit 15 at least partially disposed within body portion 11. Pressure sensor 14 is at least partially disposed within body portion 11. Integrated circuit 15 is adapted to receive a signal from pressure sensor 14 and to derive pressure measurement data from the signal. When first end 16 of body portion 11 is fastened to the fluid source and second end 12 of body portion 11 is fastened to an infant feeding nipple, conduit 13 brings the fluid source into fluid communication with the feeding nipple. Thus, when the assembled system is provided to an infant, the sucking behavior of the infant may be measured and recorded.

Body portion 11 houses and physically protects the embedded electronics of the device. Body portion 11 may also serve as a convenient means for attaching device 10 to a fluid source, such as a baby bottle. For convenience and functionality, body portion 11 may be sized in proportion to a baby bottle so that the baby bottle and attached device may be easily held by a nurse or other individual while the infant is feeding from the bottle. According to an exemplary embodiment, the volumetric size of body portion 11 is no greater than the volumetric size of a conventional 4 oz. baby bottle.

Body portion 11 may be constructed of any material or combination of materials suitable for infant feeding, clinical, and/or culinary applications. According to an exemplary embodiment, the materials of construction may include a comestible-grade metal or plastic. In some embodiments, body portion 11 may be constructed of a shapeable, more preferably moldable, thermoplastic resin such as polyethylene and the like.

Figure 2A:
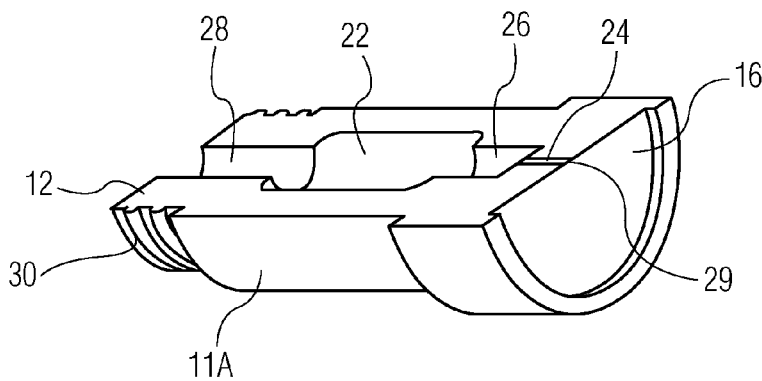
FIGS. 2A and 2B are isometric exploded view diagrams of respective top and bottom halves of a body portion of the device shown in FIG. 1.
Figure 2B:
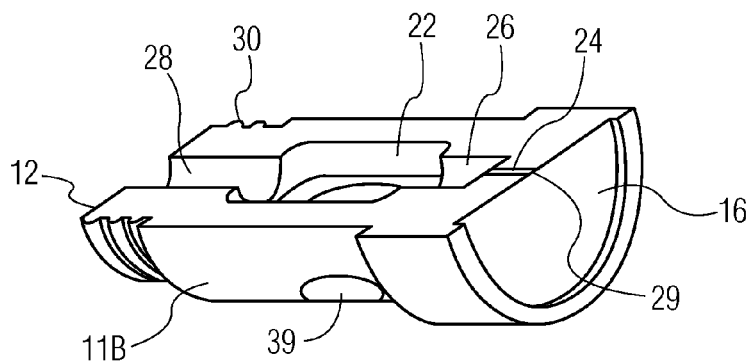
Figure 3A:
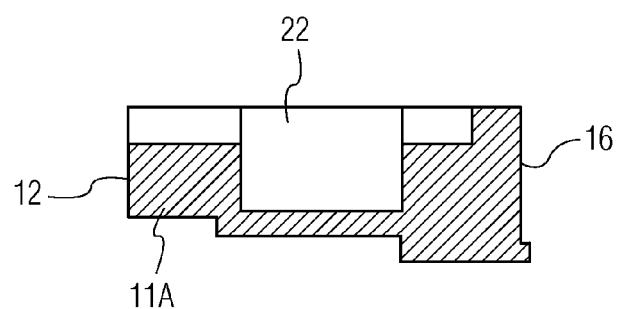
FIGS. 3A and 3B are a cross-sectional views of the body portion shown in FIG. 2.
Figure 3B:
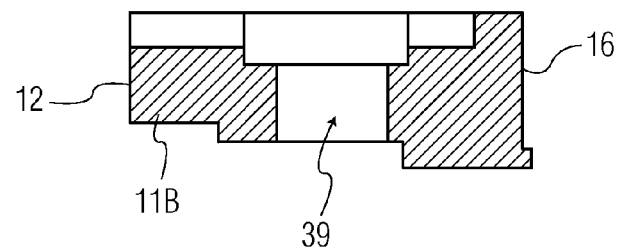
Figure 4:
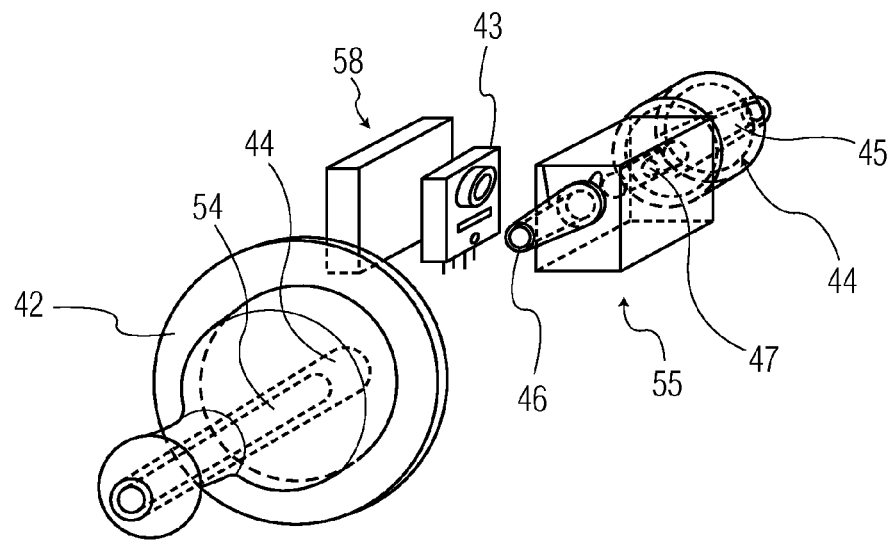
FIG. 4 is an isometric exploded view diagram of an exemplary pressure sensor assembly of the device shown in FIG. 1 in relation to a feeding nipple, according to an embodiment of the present invention.

Referring to FIGS. 2A, 2B, 3A and 3B, an example body portion 11 is further described. In particular, FIG. 2A shows an isometric view of top half 11A of body portion 11; FIG. 2B shows an isometric view of bottom half 11B of body portion 11; FIG. 3A shows a cross-sectional view of top 11A; and FIG. 3B shows a cross-sectional view of bottom half 11B. In FIGS. 2A, 2B, 3A and 3B, body portion 11 is shown, without any embedded sensors or electronics.

Body portion 11 includes first end 16 having an opening 29 that allows the ingress of fluid from a fluid source, such as a baby bottle or a collapsible bag. Device 10 optionally may include other elements to facilitate fastening first end 16 of body portion 11 to the fluid source. For example, for embodiments in which the source is a conventional baby bottle, the device may include a gasket 51 (See FIG. 5), such as a silicone gasket, to reduce the likelihood of leakage at the joint between the device and baby bottle and to provide a mechanism for allowing air (via air inlet 66, shown in FIG. 6) to enter the bottle to replace the fluid consumed by the infant during feeding. Although not shown in FIGS. 2 and 3, device 10 may include a housing to cover body portion 11. Device 10 may also include a slit valve (not shown) located in the fluid source. The slit valve may allow air to replace the fluid consumed by an infant while preventing leakage from the source. An example of a slit valve is the DU 027.001 SD valve available from Minivalve International of Jaartsveldstraat 5a, 7575 BP Oldenzaal, The Netherlands.

Example body portion 11 also includes second end 12 having a fastening mechanism 30 for releasably fastening an infant feeding nipple to the body portion. Fastening mechanism 30 may include any mechanism suitable for clinical and/or comestible use. It is desirable that fastening mechanism 30 provide a leak resistant seal to prevent fluid from leaking from the joint between body portion 11 and the feeding nipple. In some embodiments, fastening mechanism 30 includes a threaded fitting, such as a threaded fitting that is mateable to a collar for holding an infant nipple.

Referring to FIGS. 2A, 2B, 4 and 5, sections of conduit 13 in relation to capillary 53 and conduit 54 are described next. Body portion 11 includes cavity 24 for capillary 53, cavity 28 for second conduit section 46, cavity 26 for first conduit section 45 and cavity 22 for third conduit 47 (within pressure sensor housing 56). First conduit section 45 acts as a connector for linking the capillary 53 to pressure sensor 43. According to one embodiment feeding nipple may include nipple conduit 54. Second conduit section 46 may act as a connector for linking nipple conduit 54 to pressure sensor 43. According to another embodiment, feeding nipple 42 may not include a nipple conduit. Capillary 53 and nipple conduit 54 may be constructed of comestible or surgical grade silicone tubing or similar material.

Capillary 53 may be a helical capillary tube (described further with respect to FIGS. 9A through 10B) or may be a straight tube. A helical capillary tube may be formed over a smaller region as compared with a straight tube. For embodiments in which capillary 53 and nipple conduit 54 are constructed of silicone tubing or similar material, cavities 26, 28 may house a fastener for connecting respective capillary 53 and nipple conduit 54 to first and second conduit sections 45, 46. In an exemplary embodiment, a fastener for connecting the capillary 53 and nipple conduit 54 to conduit sections 45 and 46 are luer-type connectors 44. In other exemplary embodiments, first conduit section 45 may be formed from cavities 26, 28 and/or second conduit section 46 may be formed from cavity 28. That is, the hollow cavities 24, 26 and 28 may serve as respective conduit sections 45, 46 that are molded into body portion 11 themselves may serves as capillaries without the need for additional tubing. It may be desirable for cavities 22, 24, 26, 28 for respective conduit sections 45, 46 and pressure sensor 43 to be disposed along axis 19 (FIG. 1) of body portion 11.

Referring to FIGS. 2-5, a relationship between pressure sensor 43 and body portion 11 is described. Pressure sensor 43 may be considered to be part of a pressure sensor assembly 55 which also includes housing 56, hollow conduit 47, and pressure sensor support 58. Body portion 11 includes one or more cavities 22 for housing at least a portion of a pressure sensor assembly 55 and at least a portion of an integrated circuit (not shown). Cavity 22 for housing pressure sensor assembly 55 may be disposed between cavities 26, 28 for the first and second conduit sections 45, 46.

In some embodiments, cavity 22 for housing pressure sensor assembly 55 and/or the integrated circuit may be encapsulated within body portion 11. In other embodiments, cavity 22 may have at least one side exposed to the surface of the body portion. In still other embodiments, cavity 22 for housing pressure sensor assembly 55 and/or the integrated circuit may be encapsulated by the body portion and have an access port 39 extending from cavity 22 to the surface of body portion 11. In general, exposure of cavity 22 to the surface of body portion 11 may provide access to the pressure sensor assembly 55 and/or the integrated circuit.

Figure 6:
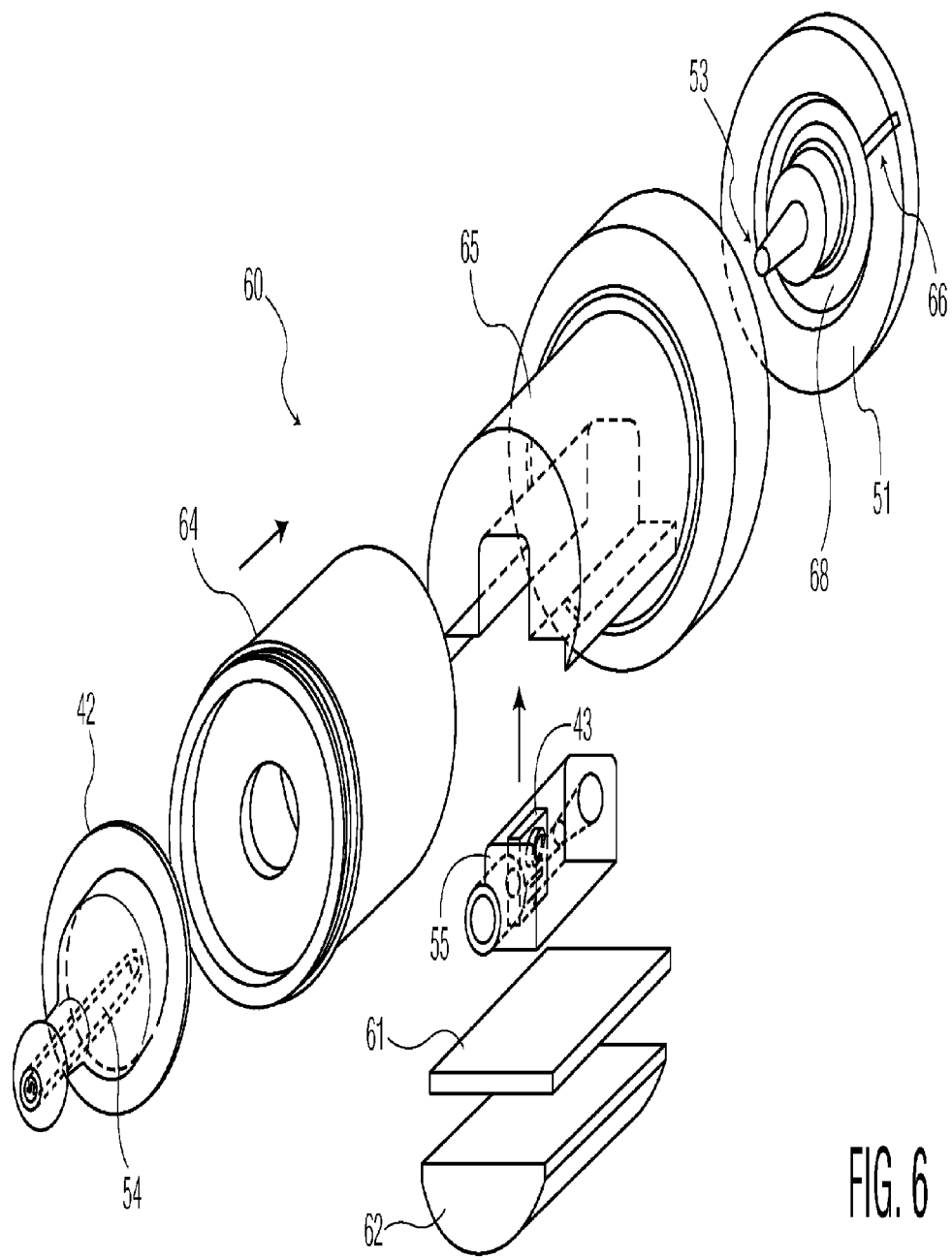
FIG. 6 is an isometric exploded view diagram of an exemplary device for measuring infant feeding performance, according to another embodiment of the present invention where the body portion comprises two mateable halves.
Figure 7:
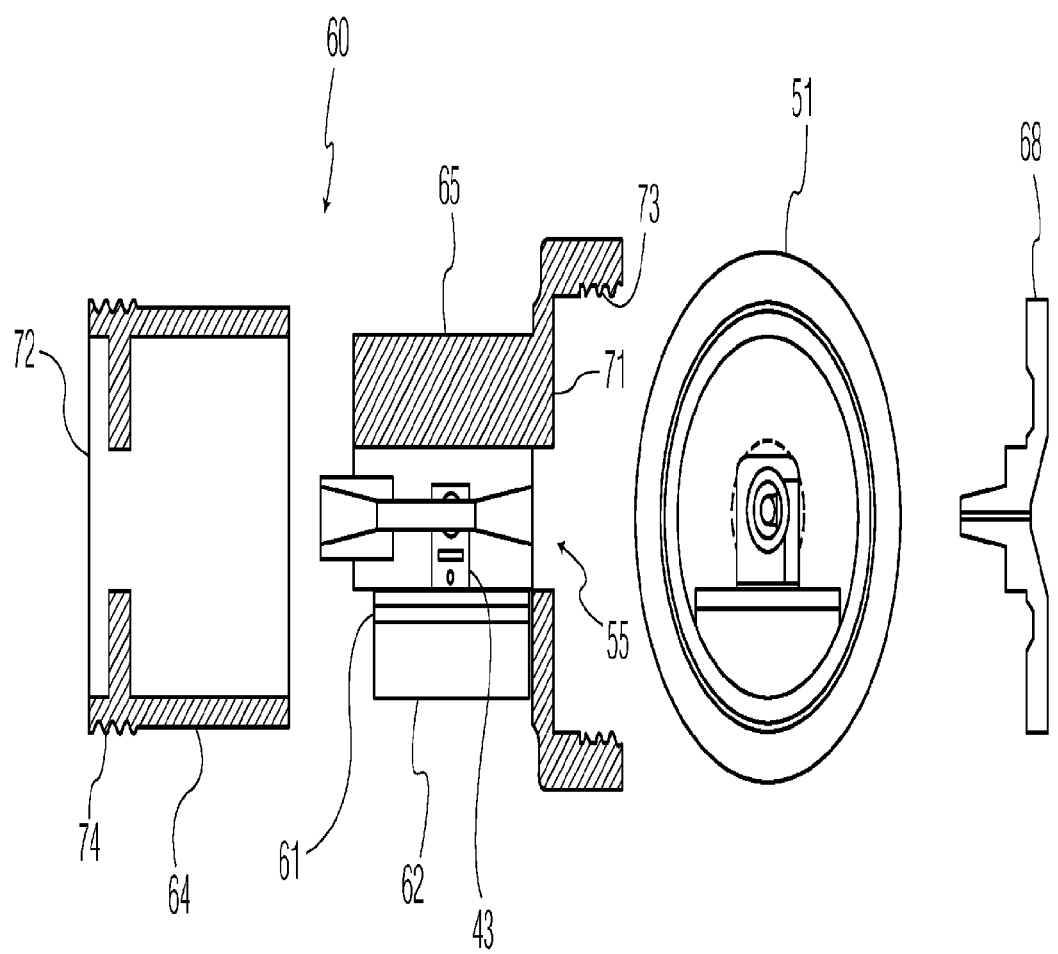
FIG. 7 is a cross-sectional view diagram of the device shown in FIG. 6.

Referring next to FIGS. 6 and 7, one exemplary method for forming body portion 60 is described. According to one exemplary embodiment, body portion 60 may be produced by conventional injection molding techniques. As shown in FIGS. 6 and 7, body portion 60 may be formed as two or more mateable sections 64, 65. Alternatively, body portion 60 can be formed as a single unit. Mateable sections 64, 65 may be temporarily or permanently fastened together to form an assembled body portion 60. Body portion 60 is also illustrated in conjunction with pressure sensor assembly 55 and embedded electronics including integrated circuit 61, battery/user interface assembly 62. Capillary 53 may be formed as part of capillary insert 68. Capillary insert 68 may be fitted with gasket 51 and inserted into mateable section 65 at end 71. Although not shown in FIGS. 6 and 7, body portion 60 may be covered by a housing.

Embodiments that utilize temporarily fastened mateable divisions may be advantageous because they can be disassembled to clean, modify, test, and/or replace one or more interior components (e.g., pressure sensor assembly 55, integrated circuit 61, battery/user interface assembly 62, and conduit sections 45, 46). Other exemplary embodiments in which body portion 60 is formed as a single unit, for example by injection molding the thermoplastic resin around the embedded electronics, may be advantageous because they can be more easily produced and may resist tampering. It is contemplated that such single unit embodiments may serve as disposable devices.

Referring back to FIGS. 2-5, the type of pressure sensor 43 that may be used with the present invention is not limited provided that it is suitable for comestible applications, is proportioned to be at least partially, more preferably wholly, disposed within its respective body portion cavity 22, and is capable of producing a suitable electronic signal. Pressure sensor 43 may be secured within body portion 11 by a friction fitting, fastener, or similar mechanism. Pressure sensor 43 may also be secured to body portion 11 using a suitable adhesive or a suitable bonding process. In addition, it may be desirable that pressure sensors 43 include those that can be economically produced en masse. According to an exemplary embodiment, suitable pressure sensors 43 may include those capable of measuring pressure over a range of about 10 mg Hg to about 300 mg Hg, with an accuracy of about ±1%.

Pressure sensor 43 may include a sensor element, a meter for measuring electrical potential, current, resistance, or similar electrical effect produced by the sensor element, and a housing. Examples of sensor elements include strain gauges, piezoresistors, and the like. In an exemplary embodiment, a change in resistance produced by a piezoresistor with applied mechanical stress may be measured using a Wheatstone bridge or similar circuit. That is, the piezoresistor produces a change in resistance that is measured by the Wheatstone bridge. The Wheatstone bridge, in turn, produces an output voltage signal that may be converted into a digital signal for further processing. Pressure sensor 43 may also include other electrical components, such as an amplifier and the like. An example of a commercially available pressure sensor includes a Freescale MPX2300 manufactured by Motorola, Inc. of Schaumburg, Ill., USA.

According to an exemplary embodiment, the signal generated by pressure sensor 43 may be digitally sampled at an appropriate rate for further analysis either by the embedded electronics or when downloaded to a remote computer. In certain embodiments, the signal generated by pressure sensor 43 may, for example, be sampled at a rate of about 100 Hz to about 1000 Hz.

Pressure sensor assembly 55 is housed within body portion 11 in a position to measure the pressure of the fluid passing through a hollow conduit 47. In an exemplary embodiment, such as the one shown in FIG. 4, pressure sensor assembly 55 is positioned along the axis of the hollow conduit 47 so that the hollow conduit 47 passes through the assembly. Pressure sensor 43 may be disposed so as to contact hollow conduit 47 and/or the conduit sections 45, 46. In some embodiments, pressure sensor assembly 55 may be fastened to the first and/or second conduit sections 45, 46 (or capillary 53 and nipple conduit 54) via luer fittings 44, such as luer locks. Such fittings may provide a substantially leak-free joint between pressure sensor assembly 55 and conduit sections 45, 46.

Figure 5:
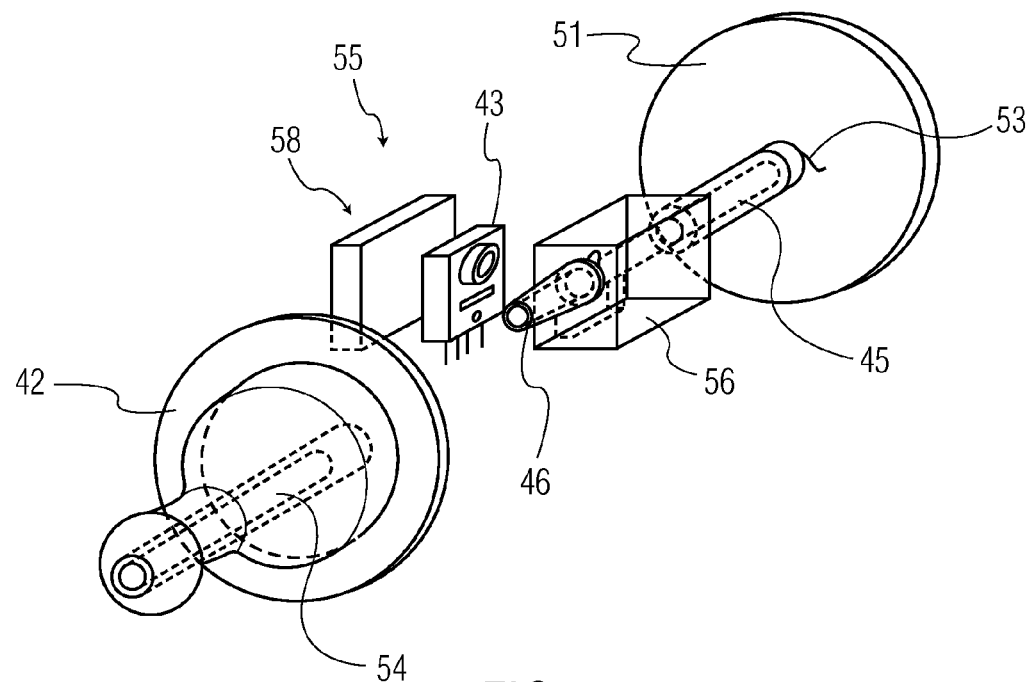
FIG. 5 is an exploded isometric view diagram of an exemplary pressure sensor assembly connected to first and second conduit sections according to an embodiment of the present invention.

Referring to FIGS. 1 and 5, according to an exemplary embodiment, first conduit section 45 has a cross-sectional area larger than the cross-sectional area of the capillary 53. Because the fluid flowing through the hollow conduit 13 encounters capillary section 53 of small cross-sectional area, a rate of fluid flow can be determined by measuring the pressure inside the capillary, for example using atmospheric pressure as a reference pressure. The fluid flow rate may then be determined from the measured pressure, for example by applying Bernoulli's principle, which describes a proportional relationship between fluid pressure and a fluid flow rate, i.e. the flow is directly proportional to the pressure differential across a given capillary. The fluid pressure and fluid flow rate may be used to determine one or more feeding factors.

Device 10 is configured to measure the sucking pressure that is applied to the tip of nipple 42 by the infant's sucking action, where the pressure is measured within conduit 13. Depending on the type of pressure sensor employed, the measured sucking pressure can be relative to either vacuum or atmospheric pressure. In either case, the fluid volumetric flow through a given capillary or other restriction increases or decreases directly with increasing or decreasing sucking pressure.

It is contemplated that the range of fluid volumetric flow may be adjusted by varying a length of capillary 53. For example, a longer capillary 53 of the same hydraulic diameter would decrease the fluid flow. Accordingly, a length of capillary 53 may be adjusted to vary the flow, for example, to account for the infant's age and/or feeding capabilities. For example, early pre-term infants may be delivered fluid at decreased flow rates (decreased flow volume) as compared to older infants. As described below with reference to FIGS. 9A through 10B, the capillary 53 may be implemented as a channel formed along the threads of a screw fitted into a threaded opening. The length of capillary 53 may be represented as $n\pi D$ where n is the number of screw turns and D is the diameter of the screw. As an example, for a 6-32 screw, the approximate length/turn is about 0.43 inches.

Referring to FIGS. 6 and 7, a signal generated by pressure sensor 43 is received by integrated circuit 61 where it is digitally converted into, and preferably stored as, sucking pressure and/or fluid volumetric flow data. Integrated circuit 61 may include one or more ADC's, microcontrollers and/or microprocessors for generating and processing the data. Integrated circuit 61 may also include one or more memory chips, such as flash memory, for storing the data. Alternatively, the ADC and memory chips may be separate from the integrated circuit 61.

In an exemplary embodiment, the electronics system, including the integrated circuit 61, may also include one or more of the following components: an analog to digital converter, a digital signal processor and a wireless communication system. Device 10 may also include battery/user interface assembly 62. A user interface may include one or more features such as buttons, indicators, an electronic display, a touch screen, a microphone, a speaker, and the like. These optional components may allow the operator to setup, control and monitor the device, provide feedback, including alarms, to the operator, and/or allow the operator to input additional data such as voice recordings or event markers correlating to observations of the operator during a feeding session. An indicator may also be used to provide feedback to the operator, such as to provide an indication of a detected clog of the fluid within device 10. In some embodiments, the microcontroller of the embedded electronics may be programmable and may analyze the data, compute trends based upon the data, and/or generate a medically relevant assessment score for the patient as a function of the sucking pressure and fluid volumetric flow data. For example, a trend of the peak sucking pressure over time may be analyzed to detect the presence of a clog.

In an exemplary embodiment, integrated circuit 61 may be embedded in body portion 60 and may be fixed by a friction fitting, adhesive, mechanical faster, or related device. In certain embodiments, integrated circuit 61 is in operative contact with a surface of body portion 60 to provide or receive information to or from an operator.

In addition to the measuring and recording of sucking pressures and/or fluid volumetric flow rates, device 10 may optionally contain additional sensors to measure other variables related to the responsiveness of the infant during a feeding session. Examples of these sensors include a flow sensor for monitoring breathing and infrared optical sensor for monitoring heart rate and/or blood oxygenation.

Figure 9A:
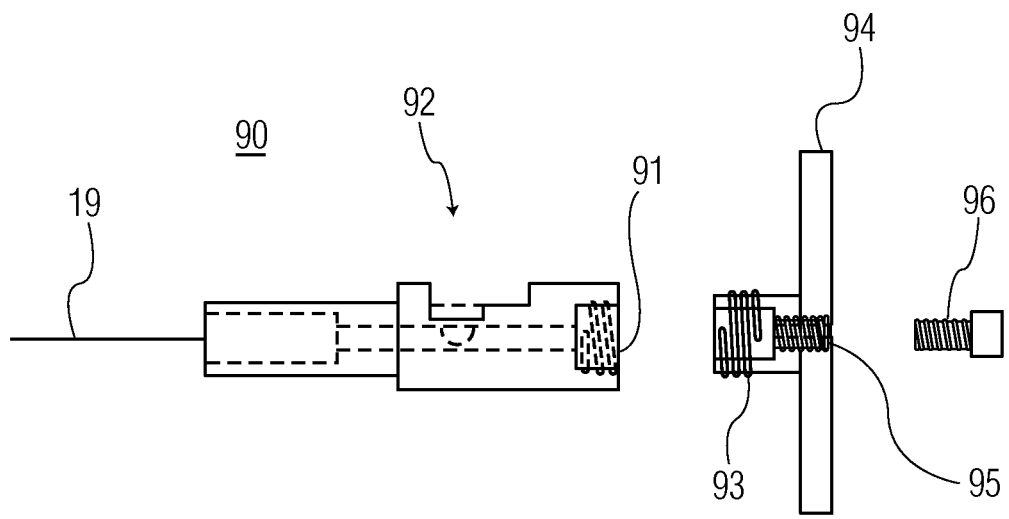
FIGS. 9A and 9B are side view diagrams of an exemplary device for measuring infant feeding performance, according to another embodiment of the present invention.
Figure 9B:
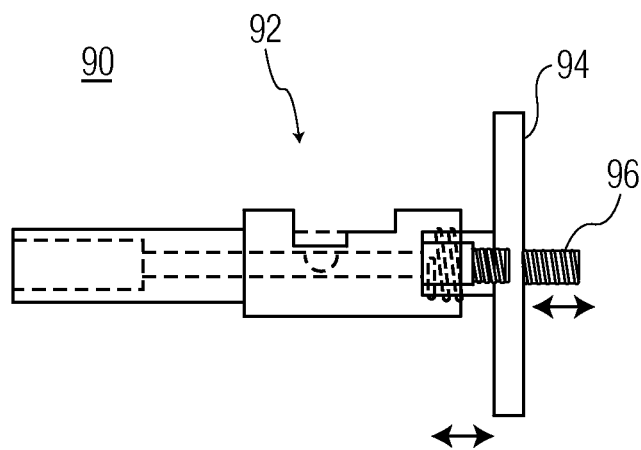

Referring to FIGS. 9A and 9B, another device 90 for measuring infant feeding performance is shown. In particular, FIG. 9A is an exploded side view diagram of device 90; and FIG. 9B is a side view diagram of device 90. In FIGS. 9A and 9B, the embedded electronics and pressure sensor assembly are not shown. In addition, although not shown in FIGS. 9A and 9B, device 90 may include a housing to cover body portion 92.

Device 90 includes body portion 92, capillary insert 94 and helical capillary 96 (as a capillary section). Capillary insert 94 and body portion 92 include respective opposing threaded fittings 91, 93, such that capillary insert 94 may be inserted into body portion 92. Capillary insert 94 includes an additional threaded fitting 95 for receiving helical capillary 96. Each of capillary insert 94 and helical capillary 96 may be rotated to adjust the length of the capillary section.

According to an exemplary embodiment, helical capillary 96 includes a threaded screw. The threaded portion may include a groove that acts as a capillary for conducting fluid into body portion 92. In an exemplary embodiment, helical capillary 96 includes screws with 32 or 40 threads per inch. Because the capillary has a helical shape, the length of the capillary (i.e., the groove) may be substantially increased along an axial direction, with little increase in the total length of helical capillary 96 relative to axis 19. As an alternative to having the capillary formed in the screw, the capillary may be formed in the threads of the capillary insert 94.

Figure 10A:
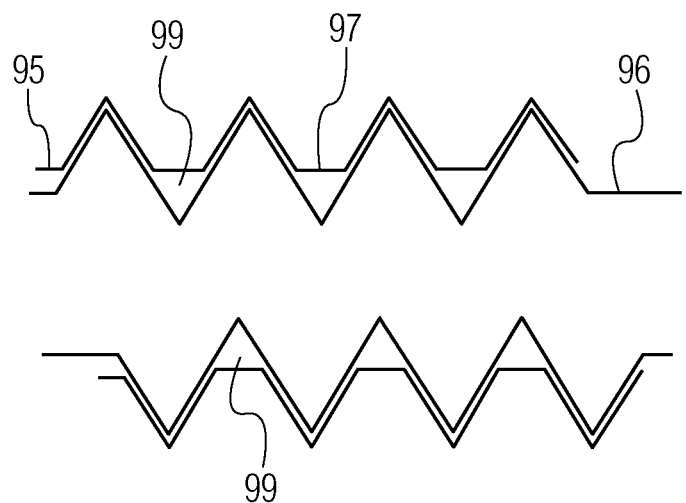
FIGS. 10A and 10B are cross-sectional view diagrams of capillary sections formed by the exemplary device shown in FIGS. 9A and 9B, according to embodiments of the present invention.
Figure 10B:
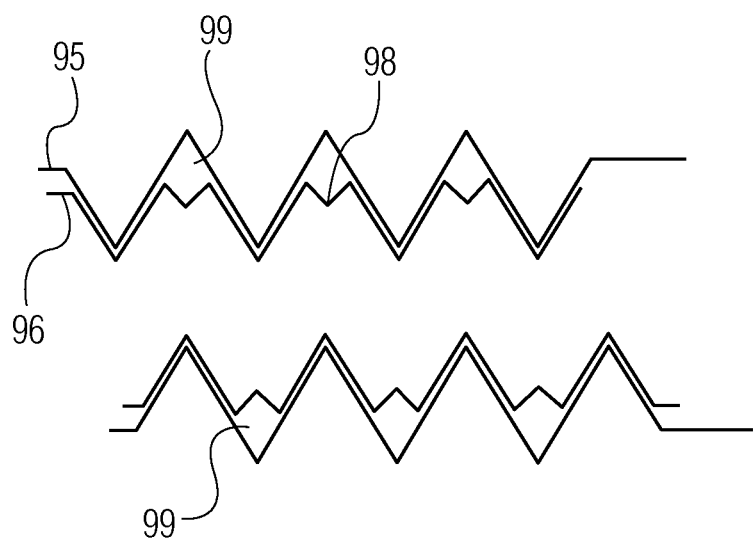

Referring to FIGS. 10A and 10B, cross-sectional view diagrams of a capillary section are shown formed between capillary insert 96 and helical capillary body 95. In this example, the capillary body 95 is a threaded aperture in capillary insert 94 and the capillary insert 96 is a screw insert. In particular, the capillary section may be formed by gap 99 between helical capillary insert 96 and female threads of capillary body 95. It is contemplated that female threads of capillary body 95 or of helical capillary insert 96 may be machined to increase a width of gap 99. As shown in FIG. 10A, female threads 95 are machined at root 97. As shown in FIG. 10B, helical capillary insert 96 is machined at crest 98. Machining of female threads of capillary body 95 or the male threads of helical capillary insert 96 may be used, for example, to decrease a resistance of the fluid flowing in the capillary section.

Referring back to FIG. 8, device 80 may be part of a system 89 for measuring and recording an infant's responsiveness to a feeding session. In addition to device 80, system 89 may include fluid source 88 for holding a comestible fluid, such as infant formula, expressed breast milk, or pediatric electrolyte solution, and an infant feeding nipple 42. Device 80 may be fastened to fluid source 88 and to feeding nipple 42 by any suitable fasteners.

Fluid source 88 may include any suitable reservoir such as a conventional baby bottle. The baby bottle may be of any conventional capacity, including, but not limited to, 4 oz. bottles and 8 oz. bottles. According to an exemplary embodiment, the baby bottle and nipple 42 may be releasably fastened to the measuring and recording device 80 via a fitting, such as a threaded fitting.

As shown in FIGS. 6 and 7, mateable section 64 may include first end 72 having a female threaded fitting 74 that is functionally equivalent to the female threaded fitting of a conventional infant nipple collar. Mateable section 65 may include a second end 71 having a male threaded fitting 73 that is functionally equivalent to the mateable end of a conventional baby bottle. Using functionally equivalent threaded fittings may allow the device to be easily fastened to conventional baby bottles and nipple collars without the need for additional mating adaptors.

Referring again to FIG. 8, in certain embodiments, system 89 may include one or more sensors 86 in addition to, or instead of, a pressure sensor. Sensors 86 may be embedded in body portion 81 and/or nipple 42 secured to body portion 81. If system 89 includes two or more sensors 86, at least one sensor 86 may be embedded in device 80. External sensors 86 which are not embedded in device 80, may be in data communication with device 80 via a wireless data transfer system and/or via a wired data transfer connection.

Preferably, each of the embedded sensors is in electronic communication with the integrated circuit. In such embodiments, the integrated circuit includes a microcontroller and/or microprocessor adapted to receive digital inputs from such signals. The data produced via these sensors may be transmitted to a remote recording device and/or may be stored in the embedded memory of device 80 for subsequent retrieval.

Examples of sensors 86, other than pressure sensors, that may be provided with system 89 include a pulse oximeter and/or infrared (IR) optical sensor mounted in feeding nipple 42. Such sensors may be used to measure the infant's blood oxygen saturation and $CO_2$ elimination, respectively, during a feeding session. For example, hemoglobin in the blood undergoes a change in optical absorbance as a function of the amount of oxygen bound to it. As the blood passes from the lungs to other parts of the body, oxygen is released from the hemoglobin producing an observable change in the compound's optical properties. These changes may be measured using an infrared source tuned to the spectral peak associated with oxygenated hemoglobin.

In an exemplary embodiment, a fiber optical element connected to both the tuned IR source and a photodetector may be placed in nipple 42. As the infant's mouth contacts nipple 42, for example, during a feeding session, the region of mouth where the nipple is located is exposed to the low level IR signal. A reflection of this signal off the infant's mouth may be received and monitored by a photodetector, from which the oxygenation level, pulse rate and other information may be derived.

In certain embodiments, the present invention includes a cap or collar for securing feeding nipple 42 to body portion 80. Preferably, an air flow channel may be installed in the collar that channels inhalation and exhalation of breath by the infant to appropriate sensors such as a pyroelectric or thermistor anemometer. Such embodiments may be suited for monitoring breathing rate as opposed to the magnitude of the inhalation or exhalation.

According to another embodiment, an infant's swallowing capacity may be obtained by attaching a piezoelectric impulse sensor to nipple 42. Electrical wires may be used to transport the current generated by compressing the nipple impulse sensor to the electronics. As the infant swallows, the tongue blocks the front of the mouth, compressing nipple 42 in the process. The resulting signal may provide useful information to the caregivers about the feeding process of the neonate.

According to certain embodiments, a chemical sensor may be attached to the surface of feeding nipple 42 that is secured to body portion 80 to detect and monitor trace chemicals and ions in the infants saliva.

According to another embodiment, detection of infant swallowing may be obtained by attaching a temperature sensor to nipple 42. If the liquid is at a different temperature than the mouth of the infant, the temperature sensor may be used to detect a sudden change in temperature in the mouth due to a release of a volume of liquid by the swallow event.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method of measuring infant feeding performance comprising:
    passing fluid to a feeding nipple through a conduit, the conduit having a first section to receive the fluid and a second section to pass the fluid to the feeding nipple, the second section having a greater cross-sectional area than the first section;
    monitoring a pressure of the fluid passing through the conduit during a feeding session at a position in the conduit between the first section and the second section; and
    determining a feeding factor from the monitored pressure over the feeding session indicative of the infant feeding performance.

2. The method according to claim 1, determining the at least one feeding factor including determining a volumetric flow rate of the fluid from the monitored pressure.

3. The method according to claim 1, wherein the feeding factor includes at least one of a fluid volumetric flow response or a sucking pressure response.

4. The method according to claim 1, wherein the first section includes a capillary section to receive the fluid and the method includes:
    changing a length of the capillary section to adjust a range of fluid volumetric flow exhibited by the fluid in the conduit.

5. The method according to claim 1, the method further comprising:
    determining a sucking pressure response during the feeding session;
    comparing the sucking pressure response to a predetermined clog response; and
    providing an indication of a clog in the conduit if the sucking pressure response matches the predetermined clog response.

6. A device for measuring infant feeding performance comprising:
    a body portion having a first end for receiving a fluid, a second end mateable with a feeding nipple, and a conduit in fluid communication with the first end and the second end;
    a pressure sensor disposed in the body portion and in contact with the fluid in the conduit, the pressure sensor configured to generate a signal representing a pressure of the fluid passing through the conduit during a feeding session; and
    an integrated circuit disposed in the body portion and electrically connected to the pressure sensor, the integrated circuit configured to receive the pressure signal and to determine a feeding factor over the feeding session indicative of the infant feeding performance;
    wherein the conduit comprises:
    a first conduit section in fluid communication with the first end, the first conduit section having a first cross-sectional area; and
    a second conduit section in fluid communication with the first conduit section and the second end, the second conduit section having a second cross-sectional area greater than the first cross-sectional area.

7. The device according to claim 6, wherein the integrated circuit includes at least one of an analog to digital converter, a microcontroller or a microprocessor.

8. The device according to claim 6, wherein the integrated circuit includes a memory chip for storing at least one of the pressure signal or the feeding factor.

9. The device according to claim 6, wherein the integrated circuit includes a wireless data transceiver or a wired data transceiver.

10. The device according to claim 6, further including a user interface integrated with the body portion and in electronic communication with the integrated circuit.

11. The device according to claim 10, wherein the user interface includes at least one of an input device, an indicator or a display.

12. The device according to claim 6, wherein determination of the feeding factor includes determining at least one of a fluid volumetric flow response or a sucking pressure response.

13. The device according to claim 6, further including a battery electrically coupled to the integrated circuit.

14. The device according to claim 6, wherein the first conduit section includes a helically-shaped capillary or a straight tube capillary.

15. The device according to claim 6, wherein at least a portion of the conduit forms the first and second conduit sections.

16. The device according to claim 6, wherein the pressure sensor is disposed between, and coupled to, at least one of the first and second conduit sections.

17. A system for measuring infant feeding performance comprising:
    a fluid source for storing a comestible fluid;
    a feeding nipple;
    a body portion disposed between and coupled to the fluid source and to the feeding nipple, the body portion including a conduit in fluid communication with the fluid source and the feeding nipple;
    a pressure sensor disposed within the body portion and configured to generate a signal representing a pressure of the fluid passing through the conduit; and
    an electronics system embedded within the body portion and electrically, connected to the pressure sensor, the electronics system configured to receive the pressure signal and to determine at least one of a sucking pressure response and a fluid volumetric flow response indicative of the infant feeding performance, wherein the conduit comprises:

a first conduit section in fluid communication with the fluid source, the first conduit section having a first cross-sectional area; and a second conduit section in fluid communication with the first conduit section and the feeding nipple, the second conduit section having a second cross-sectional area greater than the first cross-sectional area.

18. The system according to claim 17, further comprising at least one sensor selected from the group consisting of a microphone, a pulse oximeter, an infrared optical sensor, a piezoelectric anemometer, a thermistor anemometer, a $CO_2$ detector, an $O_2$ detector, a fiber optic pressure sensor, a thermocouple and a piezoelectric impulse sensor.

19. The system according to claim 18, wherein the at least one sensor is electrically coupled to the electronics system.

20. The system according to claim 17, wherein the first conduit section includes a helically-shaped capillary or a straight tube capillary.

21. The system according to claim 17, further including a user interface integrated with the body portion and in electronic communication with the electronics system.

22. The system according to claim 17, wherein the electronics system includes a memory chip for storing at least one of the pressure signal, the sucking pressure response or the fluid volumetric flow response.

23. The system according to claim 17, wherein the electronics system includes a wireless data transceiver or a wired data transceiver.

24. The device according to claim 6, wherein the pressure sensor is configured to be replaceably disposed in the body portion.

25. The system according to claim 17, wherein the pressure sensor is configured to be replaceably disposed within the body portion.

* * * * *

UNITED STATES PATENT AND TRADEMARK OFFICE
CERTIFICATE OF CORRECTION

PATENT NO. : 8,413,502 B2
APPLICATION NO. : 12/920178
DATED : April 9, 2013
INVENTOR(S) : Zemel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 183 days.

Signed and Sealed this
First Day of September, 2015

Michelle K. Lee
*Director of the United States Patent and Trademark Office*